(12) United States Patent
Thomas et al.

(10) Patent No.: US 11,033,279 B2
(45) Date of Patent: Jun. 15, 2021

(54) LIGATION CLIP WITH RETENTION FEATURES

(71) Applicant: Covidien LP, Mansfield, MA (US)

(72) Inventors: Justin Thomas, New Haven, CT (US); Eric Brown, Haddam, CT (US); Gregory R. Morck, Middletown, CT (US); Roy J. Pilletere, North Haven, CT (US); Saumya Banerjee, Hamden, CT (US); Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 227 days.

(21) Appl. No.: 16/261,803

(22) Filed: Jan. 30, 2019

(65) Prior Publication Data

US 2019/0321047 A1 Oct. 24, 2019

Related U.S. Application Data

(60) Provisional application No. 62/661,842, filed on Apr. 24, 2018.

(51) Int. Cl.
*A61B 17/122* (2006.01)

(52) U.S. Cl.
CPC .................. *A61B 17/122* (2013.01)

(58) Field of Classification Search
CPC .................. A61B 17/122; A61B 17/1227
See application file for complete search history.

(56) References Cited

U.S. PATENT DOCUMENTS

| 3,439,523 | A | 4/1969 | Wood |
| 3,713,533 | A | 1/1973 | Reimels |
| 4,076,120 | A | 2/1978 | Carroll et al. |
| 4,146,130 | A | 3/1979 | Samuels et al. |
| 4,187,712 | A | 2/1980 | Samuels et al. |
| 4,212,303 | A | 7/1980 | Nolan |
| 4,212,390 | A | 7/1980 | Raczkowski et al. |
| 4,294,355 | A | 10/1981 | Jewusiak et al. |

(Continued)

FOREIGN PATENT DOCUMENTS

| BE | 654195 A | 2/1965 |
| CN | 204839635 U | 12/2015 |

(Continued)

OTHER PUBLICATIONS

U.S. Appl. No. 62/655,854, filed Apr. 11, 2018, inventor Justin Thomas.

(Continued)

*Primary Examiner* — Shaun L David (57) ABSTRACT

A surgical ligation clip includes a first jaw and a second jaw pivotably coupled to the first jaw. The first and second jaws define first and second clamping surfaces, respectively, and have longitudinal ribs and transverse ribs that define first and second recesses on the first and second clamping surfaces. The second jaw is pivotable in relation to the first jaw from an open position to a clamped position to clamp tissue between the first and second clamping surfaces. In the clamped position, each of the longitudinal ribs on the first jaw is axially aligned with one of the longitudinal ribs on the second jaw and each of the transverse ribs on the first jaw is axially offset from each of the transverse ribs on the second jaw.

20 Claims, 5 Drawing Sheets

(56) References Cited

U.S. PATENT DOCUMENTS

| | | |
|---|---|---|
| 4,344,531 A | 8/1982 | Giersch |
| 4,346,869 A | 8/1982 | MacNeill |
| 4,361,229 A | 11/1982 | Mericle |
| 4,390,019 A | 6/1983 | LeVeen et al. |
| 4,412,617 A | 11/1983 | Cerwin |
| 4,418,694 A | 12/1983 | Beroff et al. |
| 4,449,531 A | 5/1984 | Cerwin et al. |
| 4,485,953 A | 12/1984 | Rothfuss |
| 4,487,205 A | 12/1984 | Di Giovanni et al. |
| 4,550,729 A | 11/1985 | Cerwin et al. |
| 4,696,396 A | 9/1987 | Samuels |
| 4,726,372 A | 2/1988 | Perlin |
| 4,834,096 A | 5/1989 | Oh et al. |
| 4,936,447 A | 6/1990 | Peiffer |
| 4,961,499 A | 10/1990 | Kulp |
| 4,971,198 A | 11/1990 | Mericle |
| 4,972,949 A | 11/1990 | Peiffer |
| 5,046,611 A | 9/1991 | Oh |
| 5,046,624 A | 9/1991 | Murphy et al. |
| 5,050,272 A | 9/1991 | Robinson et al. |
| 5,062,846 A | 11/1991 | Oh et al. |
| 5,100,416 A | 3/1992 | Oh et al. |
| 5,201,416 A | 4/1993 | Taylor |
| 5,279,416 A | 1/1994 | Malec et al. |
| 5,423,831 A | 6/1995 | Nates |
| 5,564,262 A | 10/1996 | Bevis et al. |
| 5,634,930 A | 6/1997 | Thornton et al. |
| 5,676,676 A | 10/1997 | Porter |
| 5,697,942 A | 12/1997 | Palti |
| 5,713,912 A | 2/1998 | Porter |
| 5,908,430 A | 6/1999 | Appleby |
| 5,921,991 A | 7/1999 | Whitehead et al. |
| 6,044,971 A | 4/2000 | Esposito et al. |
| 6,158,583 A | 12/2000 | Forster |
| 6,217,590 B1 | 4/2001 | Levinson |
| 6,228,097 B1 | 5/2001 | Levinson et al. |
| 6,273,253 B1 | 8/2001 | Forster et al. |
| 6,306,150 B1 | 10/2001 | Levinson |
| 6,419,682 B1 | 7/2002 | Appleby et al. |
| 6,421,920 B1 | 7/2002 | Jensen |
| 6,460,700 B2 | 10/2002 | Weisshaupt |
| 6,460,749 B1 | 10/2002 | Levinson et al. |
| 6,780,195 B2 | 8/2004 | Porat |
| 6,824,547 B2 | 11/2004 | Wilson, Jr. et al. |
| 6,863,675 B2 * | 3/2005 | Wilson, Jr. ........... A61B 17/122 |
| 6,880,699 B2 | 4/2005 | Gallagher |
| 7,001,412 B2 | 2/2006 | Gallagher et al. |
| 7,052,504 B2 | 5/2006 | Hughett |
| 7,131,977 B2 | 11/2006 | Fowler |
| 7,144,402 B2 | 12/2006 | Kuester, III |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,452,368 B2 | 11/2008 | Liberatore et al. |
| 7,585,304 B2 | 9/2009 | Hughett |
| 7,628,272 B2 | 12/2009 | Wiedenbein |
| 7,857,129 B2 | 12/2010 | Iaconi-Forrer et al. |
| 8,042,687 B2 | 10/2011 | Cannady |
| 8,312,992 B2 | 11/2012 | Disch |
| 8,403,138 B2 | 3/2013 | Weisshaupt et al. |
| 8,425,515 B2 | 4/2013 | Gamache et al. |
| 8,627,955 B2 | 1/2014 | Weisshaupt et al. |
| 8,839,954 B2 | 9/2014 | Disch |
| 8,888,398 B2 | 11/2014 | Werth |
| 9,220,507 B1 * | 12/2015 | Patel .................. A61B 17/064 |
| 9,271,737 B2 | 3/2016 | Castro et al. |
| 9,282,972 B1 | 3/2016 | Patel |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,517,178 B2 | 12/2016 | Chancibot |
| D808,522 S | 1/2018 | Cannady et al. |
| 9,855,053 B2 | 1/2018 | Bagaoisan et al. |
| 10,130,373 B2 | 11/2018 | Castro et al. |
| 10,136,898 B2 | 11/2018 | Schmidt et al. |
| 2002/0046961 A1 | 4/2002 | Levinson et al. |
| 2002/0177863 A1 | 11/2002 | Mandel et al. |
| 2004/0199178 A1 | 10/2004 | Small |
| 2005/0165422 A1 * | 7/2005 | Wilson, Jr. ......... A61B 17/1222 606/151 |
| 2005/0165423 A1 * | 7/2005 | Gallagher ............ A61B 17/122 606/151 |
| 2005/0165424 A1 | 7/2005 | Gallagher et al. |
| 2006/0089659 A1 | 4/2006 | Small |
| 2006/0124485 A1 | 6/2006 | Kennedy |
| 2006/0217749 A1 * | 9/2006 | Wilson, Jr. .......... A61B 17/122 606/157 |
| 2007/0083218 A1 | 4/2007 | Morris |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2009/0088783 A1 | 4/2009 | Kennedy et al. |
| 2009/0171380 A1 * | 7/2009 | Whiting ............... A61B 17/122 606/158 |
| 2011/0224700 A1 | 9/2011 | Schmidt et al. |
| 2011/0224701 A1 * | 9/2011 | Menn .................. A61B 17/1285 606/151 |
| 2011/0295290 A1 * | 12/2011 | Whitfield ............. A61B 17/122 606/158 |
| 2011/0295291 A1 | 12/2011 | Trivisani |
| 2012/0083803 A1 * | 4/2012 | Patel .................. A61B 17/1285 606/142 |
| 2012/0226291 A1 | 9/2012 | Malizia et al. |
| 2013/0245651 A1 | 9/2013 | Schmidt et al. |
| 2013/0253540 A1 | 9/2013 | Castro et al. |
| 2013/0261642 A1 | 10/2013 | Willett et al. |
| 2014/0054192 A1 | 2/2014 | Chancibot |
| 2014/0171986 A1 * | 6/2014 | Shelton, IV ......... A61B 17/122 606/157 |
| 2014/0243862 A1 | 8/2014 | Bagaoisan et al. |
| 2014/0276970 A1 | 9/2014 | Messerly et al. |
| 2016/0151068 A1 * | 6/2016 | Jensen ................. A61B 17/122 606/157 |
| 2016/0151073 A1 | 6/2016 | Castro et al. |
| 2016/0354089 A1 | 12/2016 | Whiting |
| 2017/0020530 A1 | 1/2017 | Willett et al. |
| 2017/0027576 A1 | 2/2017 | Castro |
| 2017/0238935 A1 | 8/2017 | Shi |
| 2017/0252042 A1 | 9/2017 | Kethman et al. |
| 2018/0036008 A1 | 2/2018 | Ramsey et al. |
| 2018/0168659 A1 | 6/2018 | Bagaoisan et al. |
| 2018/0185029 A1 * | 7/2018 | Lebens, III ......... A61B 17/083 |
| 2018/0221029 A1 * | 8/2018 | Menn .................. A61B 17/122 |
| 2018/0228492 A1 | 8/2018 | Aranyi et al. |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |

FOREIGN PATENT DOCUMENTS

| | | |
|---|---|---|
| DE | 10116168 A1 | 11/2001 |
| GB | 2353710 A | 3/2001 |

OTHER PUBLICATIONS

U.S. Appl. No. 62/655,882, filed Apr. 11, 2018, inventor Justin Thomas.
U.S. Appl. No. 62/676,293, filed May 25, 2018, inventor Roy J. Pilletere.
U.S. Appl. No. 62/717,958, filed Aug. 13, 2018, inventor Justin Thomas.
U.S. Appl. No. 62/721,178, filed Aug. 22, 2018, inventor Justin Thomas.
U.S. Appl. No. 16/158,368, filed Oct. 12, 2018, inventor Roy Pilletere.
U.S. Appl. No. 16/139,581, filed Sep. 24, 2918, inventor Raja Kamaraj.
U.S. Appl. No. 13/972,582, filed Aug. 21, 2013, inventor Manoj Patel.

(56) References Cited

OTHER PUBLICATIONS

U.S. Appl. No. 16/120,648, filed Sep. 4, 2018, inventor: Paul D. Richard.

* cited by examiner

LIGATION CLIP WITH RETENTION FEATURES

CROSS-REFERENCE TO RELATED APPLICATION

This application claims the benefit of and priority to U.S. Provisional Patent Application No. 62/661,842 filed Apr. 24, 2018, the entire disclosure of which is incorporated by reference herein.

BACKGROUND

1. Technical Description

The present disclosure is directed to ligation clips for sealing body vessels and, more particularly, to ligation clips that include clamping surfaces with tissue retention features for sealing body vessels.

2. Background of Related Art

Ligation clips are commonly used during a variety of surgical procedures to ligate tissue, e.g., a body vessel. Typically, ligation clips include first and second jaws that include clamping surfaces. The jaws are pivotably connected to each other at one end and are movable between open and clamped positions. When the ligation clip is applied to a portion of a body vessel, the body vessel is clamped between the clamping surfaces of the first and second jaws. After the ligation clip is applied to the body vessel, any movement of the ligation clip in relation to the body vessel may have a negative impact on the performance of the ligation clip.

A continuing need exists in the art for ligation clips that have clamping surfaces with improved retention characteristics to prevent movement of the ligation clip in relation to a body vessel after the ligation clip is applied to the body vessel.

SUMMARY

One aspect of the disclosure is directed to a ligation clip that includes a first jaw and a second jaw pivotably coupled to the first jaw. The first jaw defines a first clamping surface that supports first longitudinal ribs that extend along at least a portion of the length of the first clamping surface and first transverse ribs that extend across at least a portion of the width of the first clamping surface. The first longitudinal ribs and the first transverse ribs define first recesses on the first clamping surface. The second jaw defines a second clamping surface that supports second longitudinal ribs that extend along at least a portion of the length of the second clamping surface and second transverse ribs that extend across at least a portion of the width of the second clamping surface. The second longitudinal ribs and the second transverse ribs define second recesses on the second clamping surface. The second jaw is pivotable in relation to the first jaw from an open position to a clamped position to clamp tissue between the first and second clamping surfaces. In the clamped position, each of the first longitudinal ribs is aligned with one of the second longitudinal ribs and each of the first transverse ribs is axially offset from each of the second transverse ribs.

In embodiments, the ligation clip defines a longitudinal axis and the first and second longitudinal ribs each include a central rib that extends along the longitudinal axis and side ribs that extend along outer edges of the first and second clamping surfaces.

In some embodiments, each of the first and second transverse ribs are formed in groups of two, wherein each group of transverse ribs is spaced from adjacent groups along the respective first and clamping surfaces.

In certain embodiments, each of the transverse ribs in each group of transverse ribs is spaced closer to the other transverse rib within the group than to the transverse ribs in adjacent groups of transverse ribs.

In embodiments, each of the longitudinal ribs is defined by a radiused side wall.

In some embodiments, each of the first and second transverse ribs is defined by a radiused side wall.

In certain embodiments, the first jaw is secured to the second jaw by a living hinge.

In embodiments, the ligation clip is formed of a polymeric material.

In some embodiments, the first and second jaws support bosses that are configured to engage a clip applier.

In certain embodiments, the first jaw includes a first locking element and the second jaw includes a second locking element that is movable into engagement with the first locking element as the ligation clip is moved towards the clamped position to retain the ligation clip in the clamped position.

In embodiments, the second jaw includes a distal portion that has spaced teeth that are configured to penetrate tissue.

In some embodiments, the second jaw includes a biasing member that is positioned to engage the first locking element in the clamped position to retain the first locking element in engagement with the second locking element.

In certain embodiments, the first and second recesses are rectangular.

In embodiments, the recesses include a bottom surface, the bottom surface being defined by the radiused side walls of the first and second longitudinal ribs.

BRIEF DESCRIPTION OF THE DRAWINGS

Various exemplary embodiments of the presently disclosed ligation clip are described herein below with reference to the drawings, wherein.

DETAILED DESCRIPTION OF EMBODIMENTS

The presently disclosed ligation clip will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel. Further, the term "about" is used generally to mean plus or minus 10 percent of the disclosed parameter.

Figure 5:
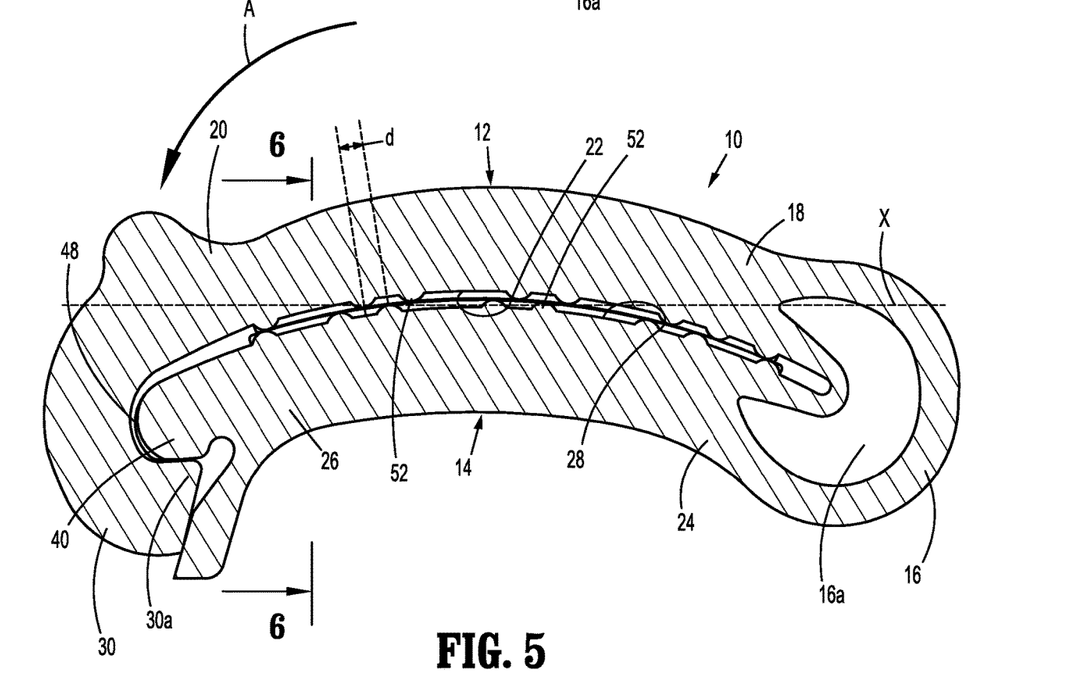
FIG. 5 is a side cross-sectional view of the ligation clip shown in FIG. 1 in the clamped position.

FIGS. 1-6 illustrate an exemplary embodiment of the presently disclosed ligation clip shown generally as 10. The ligation clip 10 defines a longitudinal axis "X" (FIG. 5) and includes a first jaw 12, a second jaw 14, and a hinge portion 16 coupling the first jaw 12 to the second jaw 14. The first jaw 12 is pivotable in relation to the second jaw 14 about the hinge portion 16 to move the ligation clip 10 between an open position (FIG. 1) and a clamped position (FIG. 5). In embodiments, the first and second jaws 12, 14 are curved along the longitudinal axis "X" of the ligation clip 10 although other jaw configurations are envisioned. The hinge portion 16 may be integrally formed with the first and second jaws 12, 14, e.g., a living hinge, and may define a crescent shaped through bore 16a to facilitate movement of the first jaw 12 in relation to the second jaw 14 between the open and clamped positions. The through bore 16a also allows for substantially complete closure of proximal portions of the first and second jaws 12, 14.

Figure 1:
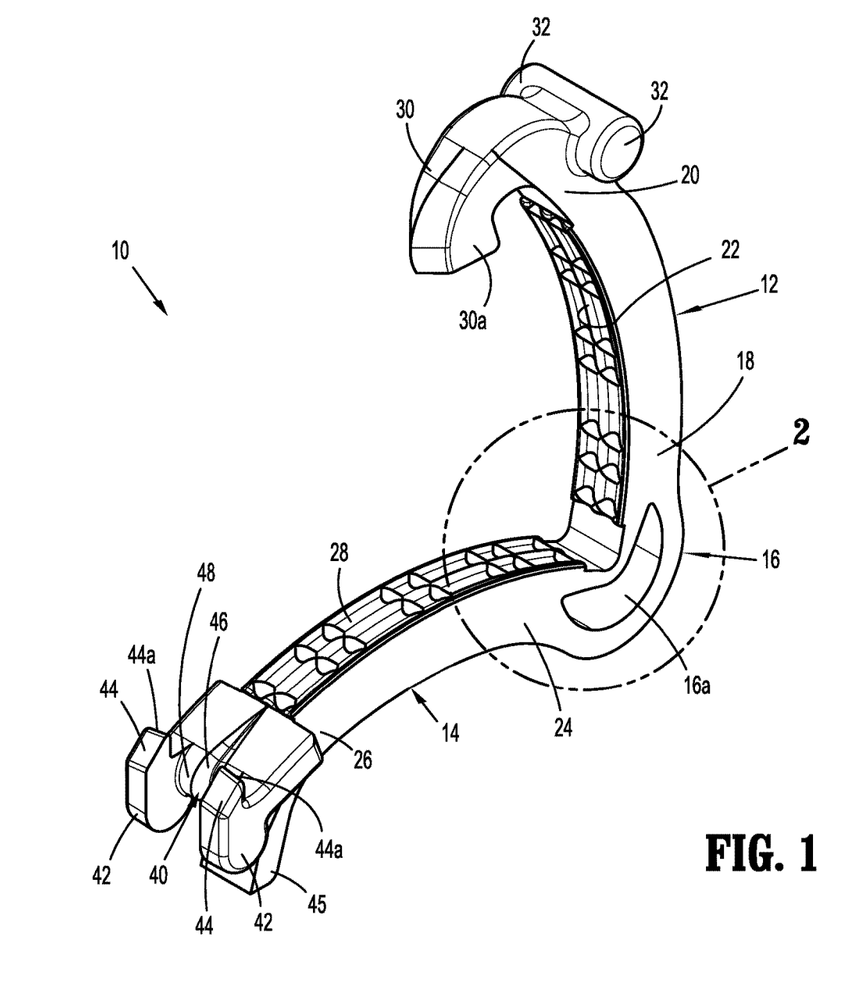
FIG. 1 is a side perspective view of an exemplary embodiment of the presently disclosed ligation clip in an open position.
Figure 2:
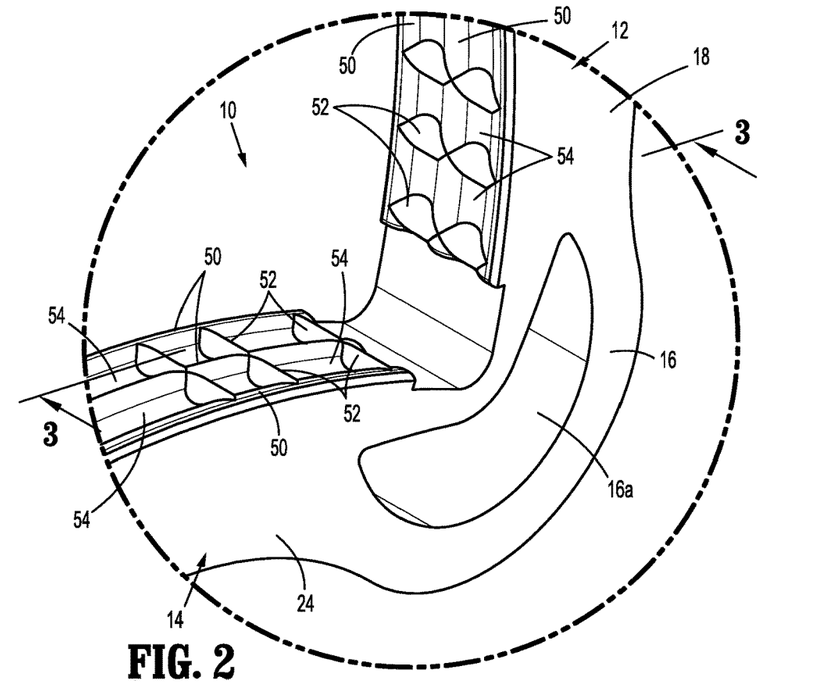
FIG. 2 is an enlarged view of the indicated area of detail shown in FIG. 1.
Figure 3:
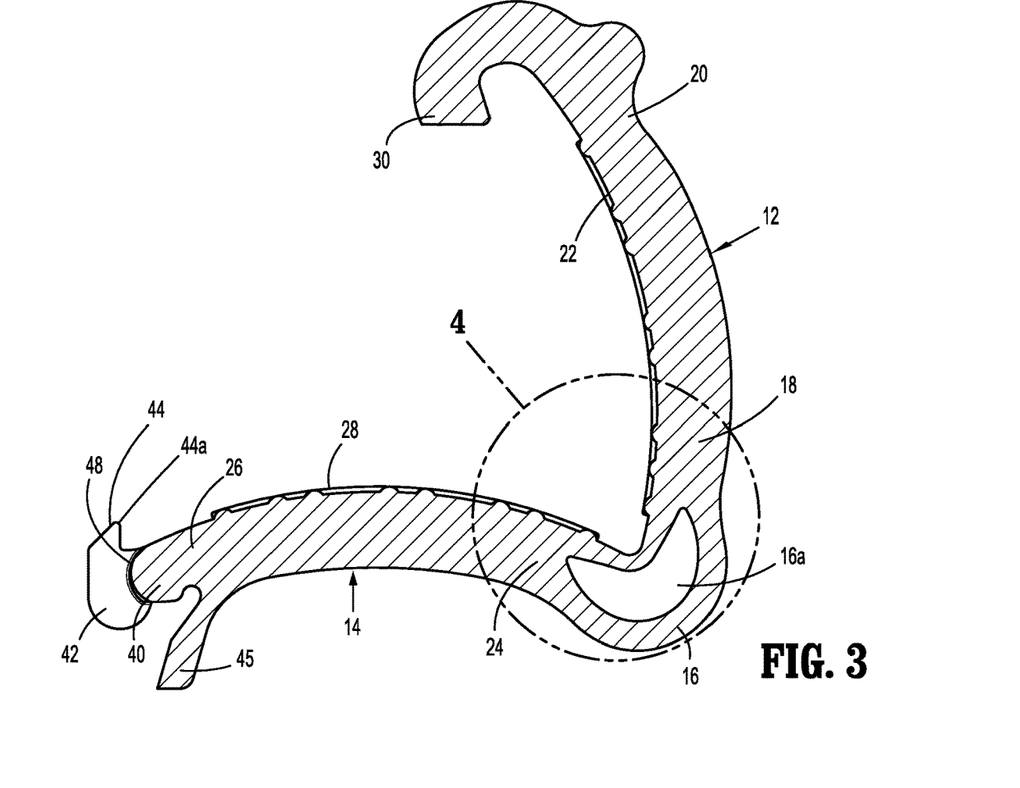
FIG. 3 is a cross-sectional view taken along section line 3-3 of FIG. 2.
Figure 4:
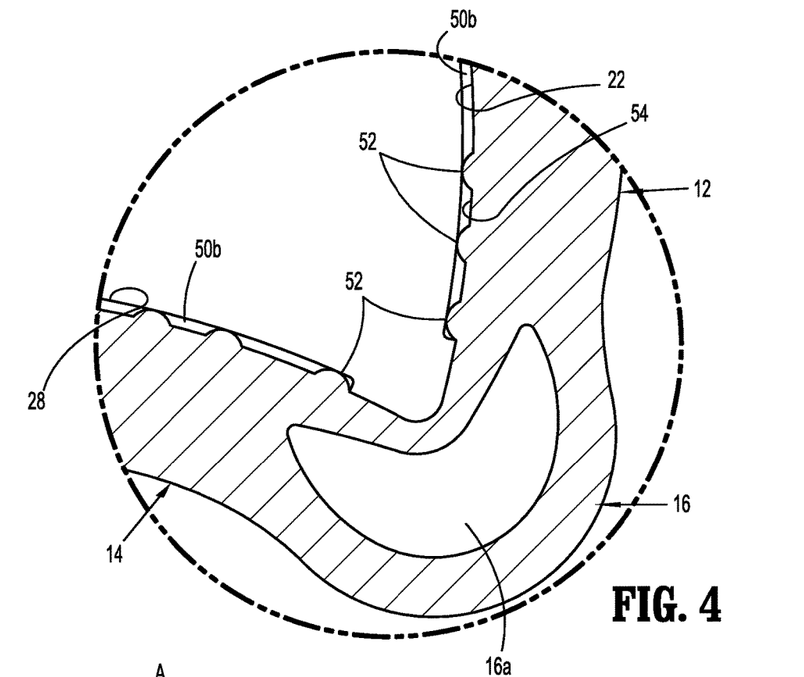
FIG. 4 is an enlarged view of the indicated area of detail shown in FIG. 3.

Referring to FIG. 1, the first jaw 12 includes a proximal portion 18, a distal portion 20, and a clamping surface 22. The second jaw 14 includes a proximal portion 24, a distal portion 26, and a clamping surface 28. The proximal portions 18, 24 of the first and second jaws 12, 14, respectively, are coupled to or integrally formed with the hinge portion 16.

Referring also to FIGS. 2-6, the distal portion 20 of first jaw 12 includes a first locking element 30 and spaced bosses 32. The first locking element 30 includes a hooked portion 30a that extends downwardly and proximally from the tissue clamping surface 22 to define a portion of a latching mechanism that is configured to retain the ligation clip 10 in a clamped position as described in further detail below. The bosses 32, which may form part of a single cylindrical member supported on the first jaw 12, are positioned and configured to engage the jaws of an applicator (not shown) to facilitate application of the ligation clip 10 to tissue.

The distal portion 26 of the second jaw 14 includes a second locking element 40, spaced bosses 42, spaced teeth 44, and a biasing member 45. The spaced teeth 44 are configured to penetrate tissue. In embodiments, the teeth 44 have an apex or pointed end 44a that grips and stretches tissue as the ligation clip 10 is moved from the open position (FIG. 1) towards the clamped position (FIG. 5) to improve the ligating characteristics of the ligation clip 10. The second locking element 40 defines a recess 46 (FIG. 1) and a cam surface 48. The cam surface 48 (FIG. 5) and the recess 46 are configured to receive and guide the first locking element 30 into locking engagement with the second locking element 40 when the ligation clip 10 is moved to the clamped position (FIG. 5) to secure the ligation clip 10 in the clamped position. In particular, the cam surface 48 is configured to deflect the first locking element 30 outwardly in a distal direction as the first locking element 30 passes over the cam surface 48 such that when the first locking element 30 moves past the cam surface 48, the first locking element 30 resiliently moves into engagement with the second locking element 40 to retain the ligation clip 10 in the clamped position. The biasing member 45 is positioned to be engaged and deformed by the second locking element 40 as the second jaw 14 is moved towards the clamped position such that the biasing member 45 resiliently urges the second locking element 40 towards the first locking element 30 to a latched position (FIG. 5). The bosses 42 of the second jaw 14 are similar to the bosses 32 of the first jaw 12 and are configured to engage jaws of an applicator (not shown) to facilitate application of the ligation clip 10 to tissue.

The first and second clamping surfaces 22, 28 each include a series of longitudinal ribs 50 and transverse ribs 52 that together define recesses 54. In embodiments, the recesses 54 can have a rectangular configuration although other configurations are envisioned. The longitudinal ribs 50 include a central rib 50a that extends along the longitudinal axis "X" (FIG. 5) of the first and second jaws 12, 14 and side ribs 50b that extend along outer edges of the clamping surfaces 22, 28 of the first and second jaws 12, 14, respectively. In embodiments, the longitudinal ribs 50 have smoothly curved or radiused side walls that define the recesses 54. The radiused side walls are atraumatic to minimize tissue damage during clamping. In embodiments, the central ribs 50a on the first and second jaws 12, 14 are axially aligned with each other, and the side ribs 50b on the first and second jaws 12, 14 are axially aligned with each other. In certain embodiments, the transverse ribs 52 on the first jaw 12 are axially offset from the respective transverse ribs 52 on the second jaw 14 such that the transverse ribs 52 on the first and second jaws 12, 14 are positioned in opposition with a recess 54 on the opposing jaw 12, 14. In some embodiments, the transverse ribs 52 on the first and second jaws 12, 14 are also formed with smoothly curved or radiused walls to minimize tissue damage during clamping.

Figure 6:
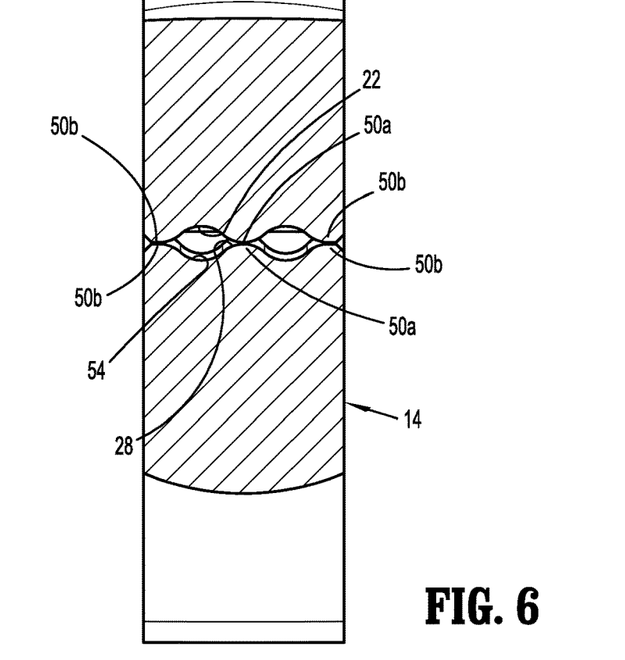
FIG. 6 is a cross-sectional view taken along section line 6-6 of FIG. 5.

Referring to FIGS. 5 and 6, when the first jaw 12 and the second jaw 14 are moved from the open position (FIG. 1) to the clamped position (FIG. 5) in the direction indicated by arrow "A" in FIG. 5, the first jaw 12 pivots in relation to the second jaw 14 about the hinge 16 to move the hooked portion 30a of the first locking element 30 into engagement with the second locking element 40 of the second jaw 14 to secure the ligation clip 10 in the clamped position. In the clamped position, the longitudinal ribs 50 (FIG. 6) of the clamping surfaces 22, 28 of the first and second jaws 12, 14, respectively, are positioned in close approximation with each other in a position to grip tissue clamped between the first and second jaws 12, 14. In contrast, the transverse ribs 52 on the first jaw 12 are axially offset from the transverse ribs 52 on the second jaw 14 (FIG. 5) and in opposition to a respective recess 54 of the opposing jaw 12, 14. The transverse ribs 52 on the first jaw 12 are positioned in close relation to one or more of the transverse ribs 52 on the second jaw 14 such that tissue is compressed between the radiused walls of the ribs 52 of the first and second jaws 12, 14. It is envisioned that the number and spacing of the longitudinal ribs 50 and the transverse ribs 52 on each of the jaws 12, 14 can be varied. In embodiments, the transverse ribs 52 are formed in groups of two ribs 52 that are spaced from adjacent groups of transverse ribs along the respective first and second clamping surfaces 22, 28. In embodiments, the spacing between two transverse ribs 52 in a group of transverse ribs 52 is less than the spacing of transverse ribs 52 from different groups. Although the transverse ribs are shown to be positioned in groups of two, the transverse ribs 52 can be singularly positioned along the clamping surfaces 22, 28 of the first and second jaws 12, 14 or the transverse ribs 52 can be formed in groups of three or more ribs 52.

In embodiments, the surgical ligation clip 10 may be comprised of a resilient bioabsorbable or biocompatible polymeric material. Examples of suitable bioabsorbable or biocompatible polymers include acetal polyoxymethylene (POM), polyethylene terephthalate (PET), polybutylene terephthalate (PBT), polyoxymethylene, polyetheretherketone (PEEK), polypropylene, and polyethylene or other thermoplastic materials having similar properties that can be injection-molded. The ligation clip 10 may also be comprised of a polymeric material or materials in combination with radiolucent metal alloys. Alternately, other materials may be used to form the ligation clip 10 including biocompatible metals, plastics and composites.

Figure 7:
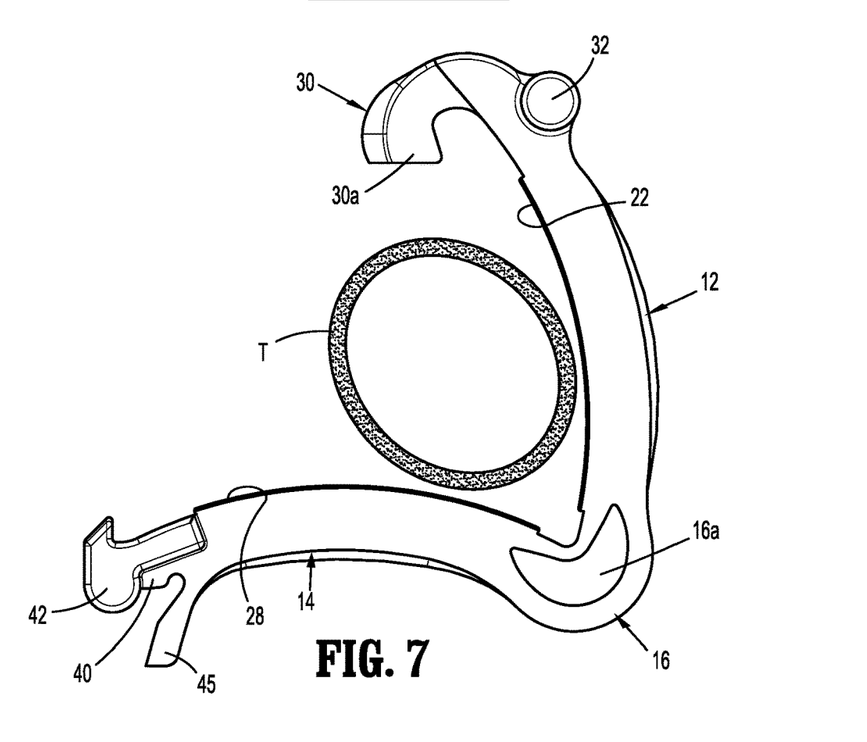
FIG. 7 is a side view of the ligation clip shown in FIG. 1 placed about tissue in the open position.
Figure 8:
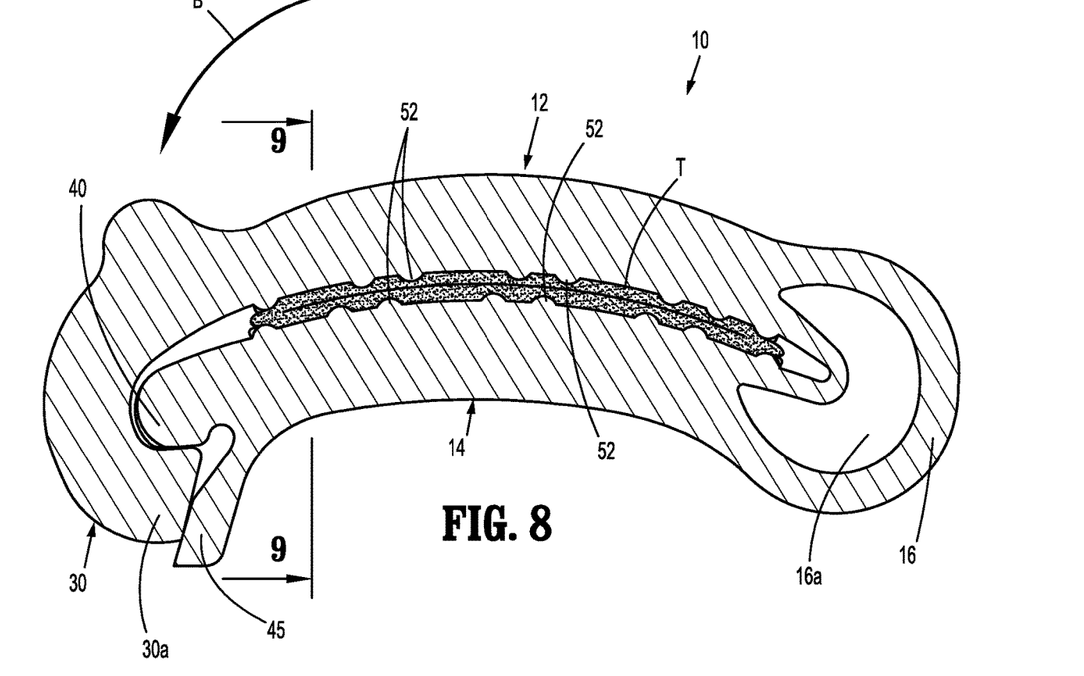
FIG. 8 side cross-sectional view of the ligation clip shown in FIG. 1 placed about tissue in the clamped position.
Figure 9:
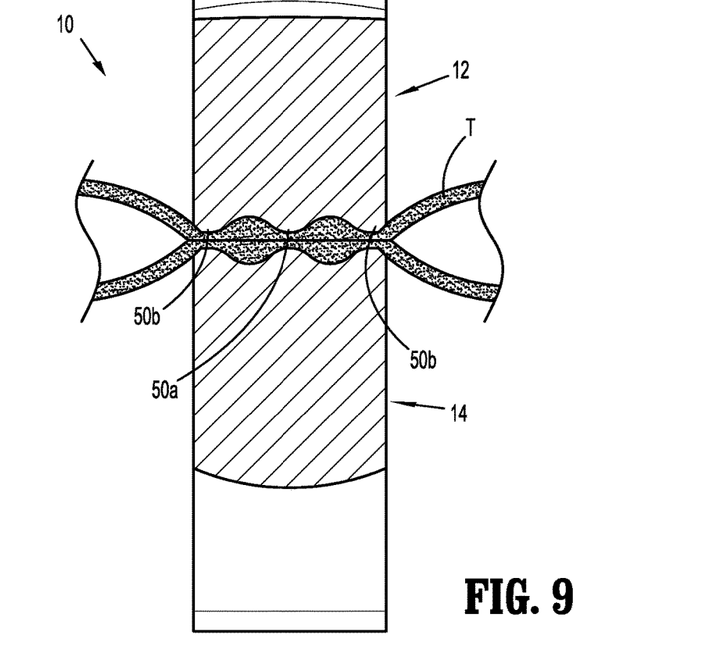
FIG. 9 is a cross-sectional view taken along section line 9-9 of FIG. 8.

Referring to FIG. 7-9, in use, the ligation clip 10 is positioned about tissue "T", e.g., a body vessel, such that the tissue "T" is positioned between the tissue clamping surface 22 of the first jaw 12 and the tissue clamping surface 28 of the second jaw 14. As described above, when the ligation clip 10 is moved from the open position (FIG. 7) to the closed position (FIG. 8) in the direction indicated by arrow "B" in FIG. 8, the first jaw 12 pivots in relation to the second jaw 14 about the hinge 16 to move the hooked portion 30a of the first locking element 30 into engagement with the second locking element 40 to secure the ligation clip 10 in the clamped position. As discussed above, the biasing member 45 engages and is deformed by the first locking element 30 to urge the first and second locking elements 30, 40 to the latched position.

As shown in FIGS. 8 and 9, in the clamped position, the tissue "T" is compressed between the first and second clamping surfaces 22, 28 of the first and second jaws 12, 14, respectively. More particularly, when the ligation clip 10 is moved to the clamped position, the tissue "T" is compressed between the longitudinal ribs 50 of the first and second jaws 12, 14. In addition, the tissue "T" is compressed between the transverse ribs 52 and a portion of the clamping surface 22, 28 of the opposing jaw 12, 14, respectively, defining the recesses 54. Finally, the tissue "T" is also compressed between the radiused side walls of the closely spaced transverse ribs 52 on opposing jaws 12, 14. As described above, this combination of compression forces improves retention of the ligation clip 10 about the tissue "T" and minimizes the likelihood that the ligation clip 10 will move in relation to the tissue "T" after placement of the ligation clip 10.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A ligation clip comprising:
   a first jaw defining a first clamping surface, the first clamping surface supporting first longitudinal ribs that extend along at least a portion of a length of the first clamping surface and first transverse ribs that extend across at least a portion of a width of the first clamping surface, the first longitudinal ribs and the first transverse ribs defining first recesses on the first clamping surface; and
   a second jaw pivotably supported in relation to the first jaw and defining a second clamping surface, the second clamping surface supporting second longitudinal ribs that extend along at least a portion of a length of the second clamping surface and second transverse ribs that extend across at least a portion of a width of the second clamping surface, the second longitudinal ribs and the second transverse ribs defining second recesses on the second clamping surface, the second jaw being pivotable in relation to the first jaw from an open position to a clamped position to clamp tissue between the first and second clamping surfaces, wherein in the clamped position, each of the first longitudinal ribs is aligned with a respective one of the second longitudinal ribs and each of the first transverse ribs is axially offset from each of the second transverse ribs, wherein a height of the first longitudinal ribs is equal to a maximum height of the first transverse ribs and a height of the second longitudinal ribs is equal to a maximum height of the second transverse ribs.

2. The ligation clip of claim 1, wherein the first jaw is secured to the second jaw by a living hinge.

3. The ligation clip of claim 1, wherein the ligation clip is formed of a polymeric material.

4. The ligation clip of claim 1, wherein the first and second jaws support bosses, the bosses being configured to engage a clip applier.

5. The ligation clip of claim 1, wherein the first jaw includes a first locking element and the second jaw includes a second locking element, the second locking element being movable into engagement with the first locking element as the ligation clip is moved towards the clamped position to retain the ligation clip in the clamped position.

6. The ligation clip of claim 5, wherein the second jaw includes a biasing member that is positioned to engage the first locking element in the clamped position to retain the first locking element in engagement with the second locking element.

7. The ligation clip of claim 6, wherein the first and second recesses are rectangular.

8. The ligation clip of claim 1, wherein each of the recesses has a bottom surface, the bottom surface being defined by the radiused side walls of the first and second longitudinal ribs.

9. A ligation clip comprising:
   a first jaw defining a first clamping surface, the first clamping surface supporting first longitudinal ribs that extend along at least a portion of a length of the first clamping surface and first transverse ribs that extend across at least a portion of a width of the first clamping surface, the first longitudinal ribs and the first transverse ribs defining first recesses on the first clamping surface; and
   a second jaw pivotably supported in relation to the first jaw and defining a second clamping surface, the second clamping surface supporting second longitudinal ribs that extend along at least a portion of the second clamping surface and second transverse ribs that extend across at least a portion of a width of the second clamping surface, the second longitudinal ribs and the second transverse ribs defining second recesses on the second clamping surface, the second jaw being pivotable in relation to the first jaw from an open position to a clamped position to clamp tissue between the first and second clamping surfaces, wherein in the clamped position, each of the first longitudinal ribs is aligned with a respective one of the second longitudinal ribs and each of the first transverse ribs is axially offset from each of the second transverse ribs;

wherein the ligation clip defines a longitudinal axis and the first and second longitudinal ribs each include a central rib that extends along the longitudinal axis and side ribs that extend along outer edges of the first and second clamping surfaces.

10. The ligation clip of claim 9, wherein each of the first and second transverse ribs are formed in groups of two, the groups being spaced from adjacent groups along each of the first and second clamping surfaces.

11. The ligation clip of claim 10, wherein each of the transverse ribs in each group of transverse ribs is spaced closer to the other transverse rib within the group of transverse ribs than to the transverse ribs in adjacent groups of transverse ribs.

12. The ligation clip of claim 9, wherein each of the longitudinal ribs is defined by a radiused side wall.

13. The ligation clip of claim 12 wherein each of the first and second transverse ribs is defined by a radiused side wall.

14. A ligation clip comprising:
a first jaw defining a first clamping surface, the first clamping surface supporting first longitudinal ribs that extend along at least a portion of a length of the first clamping surface and first transverse ribs that extend across at least a portion of a width of the first clamping surface, the first longitudinal ribs and the first transverse ribs defining first recesses on the first clamping surface; and
a second jaw pivotably supported in relation to the first jaw and defining a second clamping surface, the second clamping surface supporting second longitudinal ribs that extend along at least a portion of a length of the second clamping surface and second transverse ribs that extend across at least a portion of a width of the second clamping surface, the second longitudinal ribs and the second transverse ribs defining second recesses on the second clamping surface, the second jaw being pivotable in relation to the first jaw from an open position to a clamped position to clamp tissue between the first and second clamping surfaces, wherein in the clamped position, each of the first longitudinal ribs is aligned with a respective one of the second longitudinal ribs and each of the first transverse ribs is axially offset from each of the second transverse ribs;

wherein the second jaw includes a distal portion, the distal portion including spaced teeth that are configured to penetrate tissue.

15. A ligation clip comprising:
a first jaw defining a first clamping surface, the first clamping surface supporting first longitudinal ribs that extend along at least a portion of a length of the first clamping surface and first transverse ribs that extend across at least a portion of a width of the first clamping surface, the first longitudinal ribs and the first transverse ribs defining first recesses on the first clamping surface; and
a second jaw pivotably supported in relation to the first jaw and defining a second clamping surface, the second clamping surface supporting second longitudinal ribs that extend along at least a portion of a length of the second clamping surface and second transverse ribs that extend across at least a portion of a width of the second clamping surface, the second longitudinal ribs and the second transverse ribs defining second recesses on the second clamping surface, the second jaw being pivotable in relation to the first jaw from an open position to a clamped position to clamp tissue between the first and second clamping surfaces, wherein in the clamped position, each of the first longitudinal ribs is aligned with a respective one of the second longitudinal ribs and each of the first transverse ribs is axially offset from each of the second transverse ribs, wherein a height of the first transverse ribs does not exceed a height of the first longitudinal ribs and a height of the second transverse ribs does not exceed a height of the second longitudinal ribs.

16. The ligation clip of claim 15, wherein the first jaw is secured to the second jaw by a living hinge.

17. The ligation clip of claim 15, wherein the ligation clip is formed of a polymeric material.

18. The ligation clip of claim 15, wherein the first and second jaws support bosses, the bosses being configured to engage a clip applier.

19. The ligation clip of claim 15, wherein the first jaw includes a first locking element and the second jaw includes a second locking element, the second locking element being movable into engagement with the first locking element as the ligation clip is moved towards the clamped position to retain the ligation clip in the clamped position.

20. The ligation clip of claim 15, wherein the ligation clip defines a longitudinal axis and the first and second longitudinal ribs each include a central rib that extends along the longitudinal axis and side ribs that extend along outer edges of the first and second clamping surfaces.

* * * * *